US00PP17912P3

(12) United States Plant Patent
Jandrew

(10) Patent No.: US PP17,912 P3
(45) Date of Patent: Aug. 7, 2007

(54) ***PENSTEMON* PLANT NAMED 'PHENI PINKA'**

(50) Latin Name: *Penstemon hartwegii*
Varietal Denomination: Pheni Pinka

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/301,614

(22) Filed: Dec. 13, 2005

(65) Prior Publication Data

US 2007/0136914 P1 Jun. 14, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Georgia Helmer
(74) *Attorney, Agent, or Firm*—Jondle & Associates P.C.

(57) ABSTRACT

A new *Penstemon* plant particularly distinguished by large pink flowers with white throats and strong red markings, large inflorescences, early flowering, medium to grass-green foliage with lanceolate leaves, vigorous growth, and an upright but relatively compact plant habit with steady and stocky stems and a good branching ability is disclosed.

3 Drawing Sheets

Genus and species: *Penstemon hartwegii* Benth.
Variety denomination: 'Pheni Pinka'.

BACKGROUND OF THE NEW PLANT

The present invention comprises a new and distinct cultivar of *Penstemon,* botanically known as *Penstemon hartwegii,* and hereinafter referred to by the cultivar name 'Pheni Pinka'. The new cultivar originated from a hybridization made in 2002 in Gilroy, Calif. The female parent is a proprietary *Penstemon* plant designated '104-3' (unpatented) having blush-white flowers, and the male parent is a proprietary *Penstemon* plant designated '105-1' (unpatented) having pink flowers. The seeds produced by the hybridization were sown in November 2002, and the resulting seedlings were selected in May 2003. A single plant selection was chosen for further evaluation and for asexual propagation in the summer of 2003.

The new cultivar was created in 2002 in Gilroy, Calif. and has been asexually reproduced repeatedly by vegetative cuttings and tissue culture in Gilroy, Calif. over a three-year period. The plant has also been trialed at Gilroy, Calif., and Hillscheid, Germany. The present invention has been found to retain its distinctive characteristics through successive asexual propagations.

Plant Breeder's Rights for this cultivar were applied for in Europe on Oct. 14, 2005 and in Canada on Mar. 29, 2005.

SUMMARY OF THE INVENTION

The following are the most outstanding and distinguishing characteristics of this new cultivar when grown under normal horticultural practices in Gilroy, Calif. and Hillscheid, Germany.

1. Large pink flowers with a white throat and strong red markings;
2. Large inflorescences;

3. Early flowering;
4. Medium to grass-green foliage with lanceolate leaves;
5. Vigorous growth;
6. An upright, but relatively compact plant habit with steady and stocky stems; and
7. A good branching ability.

DESCRIPTION OF PHOTOGRAPHS

This new *Penstemon* plant is illustrated by the accompanying photographs which show blooms, buds, and foliage of the plant in full color at 15 weeks old, grown in a field in Gilroy, Calif. in June 2005; the colors shown are as true as can be reasonably obtained by conventional photographic procedures.

DESCRIPTION OF THE NEW CULTIVAR

Figure 1:
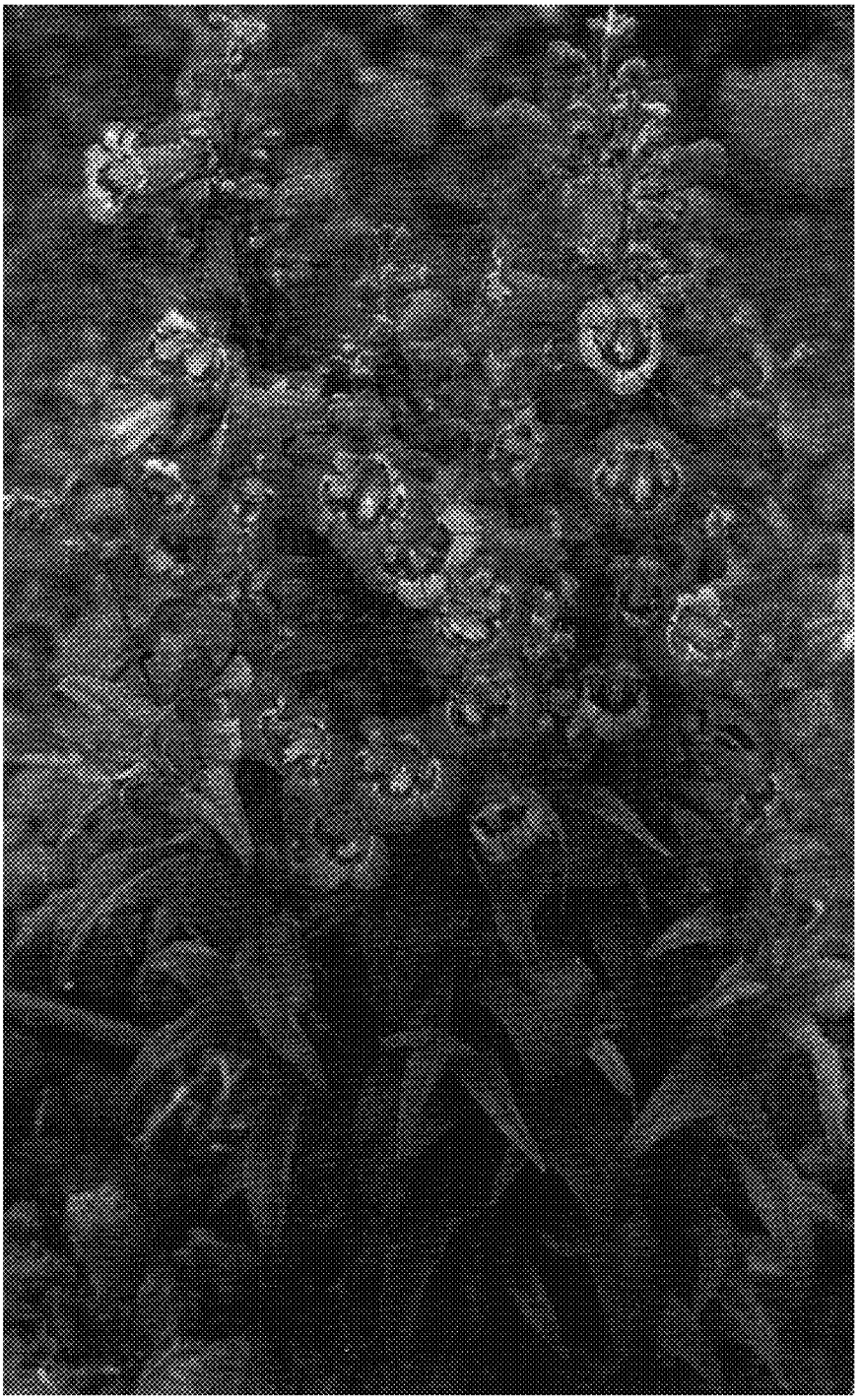
FIG. 1 shows the overall plant habit, including blooms, buds, mature foliage, and plant habit under natural light.
Figure 2:
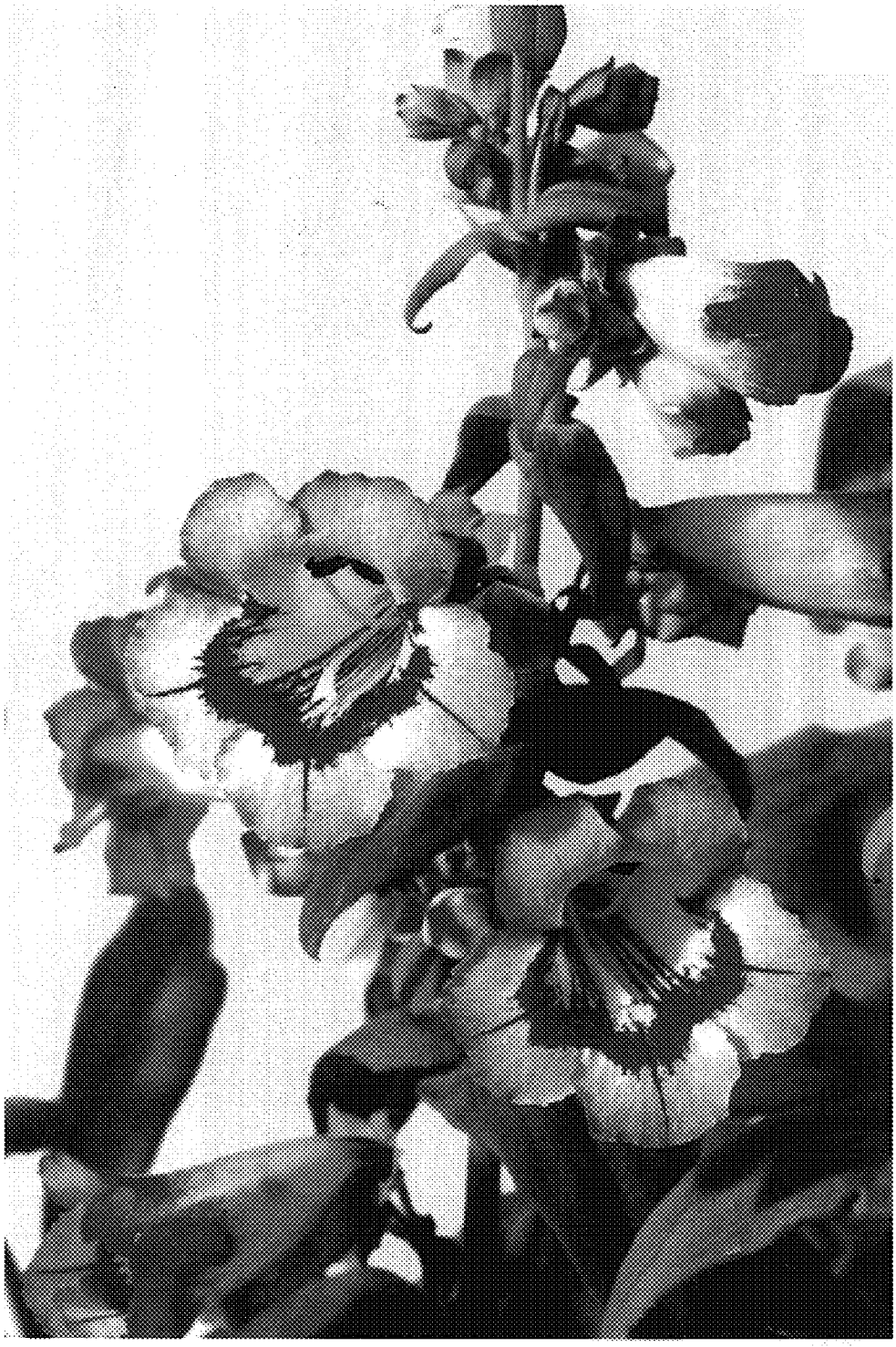
FIG. 2 shows a close-up of the mature inflorescences.
Figure 3:
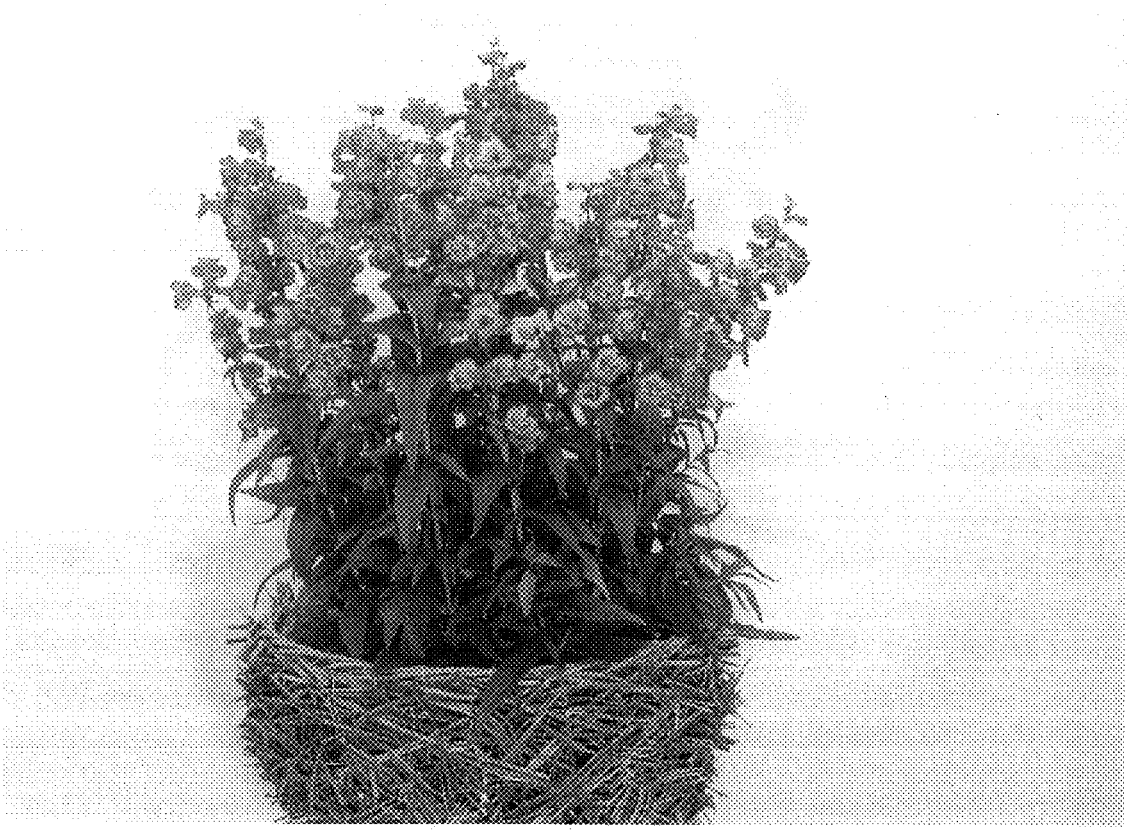
FIG. 3 shows the overall plant habit, including blooms, buds, mature foliage, and plant habit under artificial light.

The following detailed descriptions set forth the distinctive characteristics of 'Pheni Pinka'. The data which define these characteristics were collected from asexual reproductions carried out in Gilroy, Calif. The plant history was taken on nine to eleven-week-old plants grown in Hillscheid, Germany in 2005. Rooted cuttings were planted into 12-cm plastic pots placed in a greenhouse. The plants were not pinched, so they mostly developed into single-stem plant habits. Most observations were made after at the beginning of flowering. Color readings were taken under natural light. Color references are primarily to The R.H.S. Colour Chart of The Royal Horticultural Society of London (R.H.S.) (2001 edition).

DETAILED BOTANICAL DESCRIPTION OF THE NEW PLANT

Classification:

*Family.*—Scrophulariaceae.

*Botanical name.*—*Penstemon hartwegii* Benth.

Parentage:

*Female parent.*—'104-3' a proprietary blush-white-flowered *Penstemon* plant (unpatented).

*Male parent.*—'105-1' a proprietary pink-flowered *Penstemon* plant (unpatented).

Growth:

*Form.*—Herbaceous perennial; suffrutescent; tolerates only slight frost; usually cultivated as an annual plant.

*Habit.*—Un-pinched plants develop one flowering main stem without any secondary branches at the base; for commercial purposes, the plants should be pinched so that 5-10 stems of equal size will develop.

*Height.*—71 cm (as measured from the soil to the tip, including the inflorescence).

*Width.*—16 cm.

*Time to produce a finished flowering plant.*—10-11 weeks for a single-stem plant in a 5-inch pot; 13 weeks for a branched plant.

*Outdoor plant performance.*—Use in garden beds or in container planting.

*Time to initiate and develop roots.*—21 days.

*Root description.*—Somewhat fleshy at the base and mainly fibrous.

Leaves:

*Arrangement.*—Opposite and decussate.

*Shape.*—Lanceolate.

*Apex.*—Acute.

*Base.*—Sessile.

*Margin.*—Very shallowly crenate with very short bristles.

*Immature.*—Color: Upper surface: RHS 143A. Lower surface: RHS 138B. Texture: With sparse pubescence.

*Mature* (*fully expanded*).—Length: 16.0 cm. Width: 4.8 cm. Color: Upper surface: RHS 137D to RHS 143A. Lower surface: RHS 138A to RHS 138B. Texture: Smooth and appears glabrous.

*Venation.*—Type: Pinnate, midrib protruding on the lower surface. Color: RHS 145B.

Stems:

*Length.*—Approximately 45 cm as measured from the base, excluding the inflorescence.

*Diameter.*—0.6 cm as measured at the midpoint.

*Internode length.*—4-5 cm.

*Color.*—RHS 144B (light green) at the medium part.

*Texture.*—With sparse pubescence.

*Anthocyanin.*—Absent.

Flower bud:

*Shape.*—Tube-shaped with a closed end.

*Diameter.*—1.3 cm.

*Length.*—3.5 cm.

*Color* (*at tight bud*).—RHS 1D with RHS 52C at the tip.

Inflorescence:

*Inflorescence type.*—Narrow thyrse, with short peduncles bearing 4-6 flowers or buds a various stages of development.

*Blooming habit.*—Intermittent; removing of spent flowers enhances new flowering.

*Quantity of inflorescence per plant.*—One (per single stem plant).

*Lastingness of individual blooms on the plant.*—About 5 days.

*Fragrance.*—None.

*Inflorescence length.*—About 30 cm.

*Inflorescence diameter.*—11 cm.

*Peduncle.*—Color: RHS 145A (light green). Length: 2-4 cm. Diameter: 0.2-0.3 cm. Texture: Pubescent (densely covered with short hair).

Flower:

*Type.*—Zygomorphic and single; funnel-shaped with the petals mainly fused, 5-lobed with free petal lobes opening outward.

*Floret quantity* (*per inflorescence*).—About 25-30.

*Shape.*—Funnel-shaped.

*Floret diameter.*—Approximately 4.0 cm.

*Floret length* (*or depth*).—4.5 cm.

*Color.*—General: Light pink with a deeper pink margin and strong red markings. Corolla lobes: RHS 65B and near margin RHS 58C (deeper pink). Funnel (outer surface): RHS 52C (pink) to RHS 56D (nearly white). Corolla (inside color): RHS 155A (white) with RHS 53B (dark red) veins and a ring of RHS 46B (brilliant red).

*Petals* (*lobes*).—Quantity: 5. Arrangement: Two upper lobes with two lateral lobes and one lower lobe. Apex: Rounded. Base: Fused and funnel-shaped. Margin: Appears somewhat wavy, as if crenate. Texture: Smooth.

*Upper lobes, size.*—Length (from the Corolla opening): 1.1 cm. Width: 1.5 cm.

*Lateral lobes, size.*—Length (from the Corolla opening): 1.2 cm. Width: 1.9 cm.

*Lower lobe.*—Length (from the Corolla opening): 1.1 cm. Width: 2.0 cm.

*Sepals.*—Quantity: 5, in an overlapping arrangement. Color: RHS 144A. Length: 1.1 cm. Width: 0.8 cm. Shape: Ovate. Apex: Acute. Base: Attenuate. Margin: Mostly entire, a few notches may appear at the upper end. Anthocyanin: Absent. Texture: Covered with pubescence.

*Pedicels.*—Color: RHS 144A. Length: Up to 1.2 cm. Diameter: 0.2 cm. Texture: Covered with short pubescence.

Reproductive organs:

*Stamens.*—Quantity: 5 total, of which 4 are fertile. Filament: Color: RHS 155D (white). Length: 2.7-3.2 cm. Diameter: 0.1 cm. Anther color: RHS N186A (nearly black). Pollen amount: Abundant. Pollen color: 4D (pale yellow).

*Pistils.*—Quantity: 1. Length: 3.2 cm. Stigma color: RHS 145D (greenish-white). Style color: RHS 155D (white) and near the base is RHS 65B (light pink).

Fruit and seed set: Plants are fertile; frequently, the ovary is ovate, 0.6 cm in length and 0.4 cm in diameter; when the corolla drops, the ovary develops into a seed capsule (ovate) of about 1.1 cm in length and 0.7 cm in diameter.

*Seed.*—Color: RHS 200C. Shape: Irregularly round (a few more oblong), wrinkled and pitted. Diameter: 0.15 cm.

Disease and insect resistance: Has not been observed.

COMPARISON WITH PARENTAL AND COMMERCIAL CULTIVARS

'Pheni Pinka' differs from the female parent, proprietary *Penstemon* plant '104-3' (unpatented), in that 'Pheni Pinka' has pink flowers with strong red markings, while '104-3' has blush white flowers. Additionally, 'Pheni Pinka' has deeper green leaves and a more highly branched plant habit than '104-3'.

'Pheni Pinka' differs from the male parent, proprietary *Penstemon* plant '105-1' (unpatented), in that 'Pheni Pinka' has deeper pink colored flowers with darker throats than does '105-1'. Additionally, 'Pheni Pinka' flowers earlier than '105-1'.

'Pheni Pinka' differs from commercial cultivar 'Cathedral Hot Rose' (patent status unknown) in that 'Pheni Pinka' has larger pink to light pink flowers with strong red markings than 'Cathedral Hot Rose'. Additionally, 'Pheni Pinka' has a more compact plant habit and flowers earlier than 'Cathedral Hot Rose'.

I claim:

1. A new and distinct cultivar of *Penstemon* plant as shown and described herein.

* * * * *